(12) United States Patent
Gustafsson et al.

(10) Patent No.: US 7,186,718 B2
(45) Date of Patent: Mar. 6, 2007

(54) PIPERIDINYL-MORPHOLINYL DERIVATIVES AS MODULATORS OF CHEMOKINE RECEPTOR ACTIVITY

(75) Inventors: Jörgen Gustafsson, Lund (SE); Nafizal Hossain, Lund (SE); Stinabritt Nilsson, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

(21) Appl. No.: 10/486,505

(22) PCT Filed: Aug. 21, 2002

(86) PCT No.: PCT/SE02/01487

§ 371 (c)(1),
(2), (4) Date: Feb. 11, 2004

(87) PCT Pub. No.: WO03/018576

PCT Pub. Date: Mar. 6, 2003

(65) Prior Publication Data

US 2004/0204408 A1    Oct. 14, 2004

(30) Foreign Application Priority Data

Aug. 22, 2001  (GB) ................................. 0120461.9

(51) Int. Cl.
*A61K 31/5377* (2006.01)
*C07D 413/04* (2006.01)

(52) U.S. Cl. .................... 514/235.5; 544/129; 544/141
(58) Field of Classification Search .................... None
See application file for complete search history.

(56) References Cited

U.S. PATENT DOCUMENTS

| 4,695,575 | A | 9/1987 | Janssens et al. |
| 5,883,096 | A | 3/1999 | Lowe et al. |
| 5,889,006 | A | 3/1999 | Lowe et al. |
| 5,952,349 | A | 9/1999 | Asberom et al. |
| 5,977,138 | A | 11/1999 | Wang et al. |
| 6,066,636 | A | 5/2000 | Kozlowski et al. |
| 6,387,930 | B1 | 5/2002 | Baroudy et al. |
| 6,440,440 | B1 | 8/2002 | Meerpoel et al. |
| 6,903,115 | B2 | 6/2005 | Rigby et al. |

FOREIGN PATENT DOCUMENTS

| EP | 0 099 139 | 1/1984 |
| EP | 121972 A2 * | 10/1984 |
| EP | 0 145 037 | 6/1985 |
| EP | 0 151 824 | 8/1985 |
| EP | 0 151 826 | 8/1985 |
| EP | 1 076 055 | 2/2001 |
| GB | 1250719 | 10/1971 |
| WO | WO 93/10091 | 5/1993 |
| WO | WO 95/08535 | 3/1995 |
| WO | WO 96/26196 | 8/1996 |
| WO | WO 96/34857 | 11/1996 |
| WO | WO 96/41631 | 12/1996 |
| WO | WO 97/24324 | 7/1997 |
| WO | WO 98/01425 | 1/1998 |
| WO | WO 98/05291 | 2/1998 |
| WO | WO 98/05292 | 2/1998 |
| WO | WO 98/06697 | 2/1998 |
| WO | WO 98/11128 | 3/1998 |
| WO | WO 99/04794 | 2/1999 |
| WO | WO 99/37304 | 7/1999 |
| WO | WO 99/38514 | 8/1999 |
| WO | WO 99/51578 | 10/1999 |
| WO | WO 00/00488 | 1/2000 |
| WO | WO 0012478 | 3/2000 |
| WO | WO 00/32590 | 6/2000 |
| WO | WO 00/35877 | 6/2000 |
| WO | WO 00/66559 | 11/2000 |
| WO | WO 01/02381 | 1/2001 |
| WO | WO 01/07436 | 2/2001 |
| WO | WO 01/29066 | 4/2001 |
| WO | WO 01/77101 | 10/2001 |
| WO | WO 01/92227 | 12/2001 |
| WO | WO 02/18335 | 3/2002 |
| WO | WO 02/20484 | 3/2002 |
| WO | WO 02/079190 | 10/2002 |
| WO | WO 02/081449 | 10/2002 |
| WO | WO 03/004487 | 1/2003 |

(Continued)

OTHER PUBLICATIONS

Hermans, B., et al., "4-Substituted Piperidines. II. Reaction of 1-Benzyl-4-cyano-4-t-aminopiperidines with Organometallic Compounds," J. Med. Chem., vol. 8(6), pp. 851-855-(Nov. 1965), at p. 852 ("compound 12" in Table I).*
Allain et al, (2005) STN International, HCAPLUS Database, Columbus, OH, Accession No. 1992:187881, Reg. No. 46817-91-8, citing "Antidepressants and cognition: comparative effects of moclobemide, viloxazine and maprotiline," Psychopharmacology, 106(Suppl.).*
Cohen et al., *Am. J. Clin. Pathol.*105:589 (1996).

(Continued)

*Primary Examiner*—Joseph K. McKane
*Assistant Examiner*—Andrew B. Freistein
(74) *Attorney, Agent, or Firm*—Fish & Richardson P.C.

(57) ABSTRACT

The invention provides compounds of general formula (I), in which m, n, $Z^1$, $Z^2$, $R^1$, $R^2$, $R^3$, $R^4$ and $R^5$ are as defined in the specification; processes for their preparation; pharmaceutical compositions containing them; and their use in therapy (I)

15 Claims, No Drawings

FOREIGN PATENT DOCUMENTS

| WO | WO 03/024962   | 3/2003  |
|----|----------------|---------|
| WO | WO 03/078395   | 9/2003  |
| WO | WO 03/078421   | 9/2003  |
| WO | WO 2004/029041 | 4/2004  |
| WO | WO 2004/085423 | 10/2004 |
| WO | WO 2004/087659 | 10/2004 |
| WO | WO 2004/099144 | 11/2004 |

OTHER PUBLICATIONS

Patani and LaVoie, "Bioisosterism: A Rational Approach in Drug Design", *Chem. Rev.*96:3147-3176 (1996).

STN International, File CAPLUS, CAPLUS accession no. 1988:630911, Document no. 109:230911, Lehmann, Jochen et al: "Lactones. XVIII. Synthesis of lactone-bridged 1,1-diarylpropanamines"; & *Arch. Pharm.*(Weinheim, Ger.) (1988), 321(7), 443-445.

\* cited by examiner

PIPERIDINYL-MORPHOLINYL DERIVATIVES AS MODULATORS OF CHEMOKINE RECEPTOR ACTIVITY

This application claims priority under 35 U.S.C. §371 to a national phase filing of international application number PCT/SE02/01487, filed Aug. 21, 2002, which claims priority to GB 0120461.9, filed Aug. 22, 2001. These applications are incorporated by reference herein.

The present invention relates to novel compounds, processes for their preparation, pharmaceutical compositions containing them and their use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8–14 kDa proteins characterised by a conserved four cysteine motif. The chemoline superfamily can be divided into two main groups exhibiting characteristic structural motifs, the Cys-X-Cys (C-X-C) and Cys-Cys (C—C) families. These are distinguished on the basis of a single amino acid insertion between the NH-proximal pair of cysteine residues and sequence similarity.

The C-X-C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils such as human monocyte chemotactic proteins 1–3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10, CXCR1, CXCR2, CXCR3 and CXCR4. These receptors represent good targets for drug development since agents which modulate these receptors would be useful in the treatment of disorders and diseases such as those previously mentioned.

In accordance with the present invention, there is therefore provided a compound of general formula

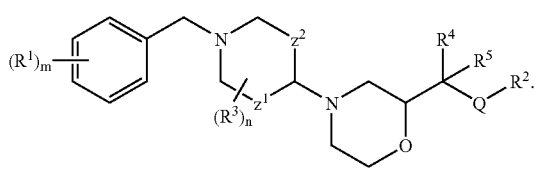

(I)

wherein
m is 0, 1, 2 or 3;
each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^6R^7$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido (—$SO_2NH_2$), $C_1$–$C_6$ alkylsulphonyl, —$C(O)NR^8R^9$, —$NR^{10}C(O)$—$(NH)_pR^{11}$, phenyl, or $C_1$–$C_6$ alkyl optionally substituted by at least one substituent selected from carboxyl and $C_1$–$C_6$ alkoxycarbonyl;

$Z^1$ represents a bond or a group $(CH_2)_q$ where q is 1 or 2;
$Z^2$ represents a bond or a group $CH_2$, with the proviso that $Z^1$ and $Z^2$ do not both simultaneously represent a bond;
Q represents an oxygen or sulphur atom or a group $CH_2$ or NH;
$R^2$ represents an unsaturated 5- to 10-membered ring system which may comprise at least one ring heteroatom selected from nitrogen, oxygen and sulphur, the ring system being optionally substituted by at least one substituent selected from halogen, cyano, oxo, nitro, carboxyl, hydroxyl, $C_2$–$C_6$ alkenyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —$NR^{12}R^{13}$, $C_3$–$C_6$ cycloalkylamino, $C_1$–$C_6$ alkylthio, $C_1$–$C_6$ alkylcarbonyl, phenylcarbonyl, $C_1$–$C_6$ alkylcarbonylamino, sulphonamido (—$SO_2NH_2$), $C_1$–$C_6$ alkylsulphonyl, —$C(O)NR^{14}R^{15}$, $C_1$–$C_6$ alkoxycarbonyl$C_1$–$C_6$ alkyl, phenyl, methyltetrazolyl, —$NHSO_2CH_3$, —$NHC(O)NR^{16}R^{17}$, $OC(O)NR^{18}R^{19}$, —$OCH_2C(O)NR^{20}R^{21}$, —$NHC(O)OR^{22}$, —$NHC(O)R^{23}$ and $C_1$–$C_6$ alkyl itself optionally substituted by at least one substituent selected from carboxyl and $C_1$–$C_6$ alkoxycarbonyl;
n is 0, 1 or 2;
each $R^3$ independently represents a $C_1$–$C_6$ alkyl, $C_1$–$C_6$ alkoxycarbonyl, —$CH_2OH$ or carboxyl group;
$R^4$ and $R^5$ each independently represent a hydrogen atom or a $C_1$–$C_6$ alkyl group;
$R^6$ and $R^7$ each independently represent a hydrogen atom or a $C_1$–$C_6$ alkyl group, or $R^6$ and $R^7$ together with the nitrogen atom to which they are attached form a 4- to 7-membered saturated heterocycle;
$R^8$ and $R^9$ each independently represent a hydrogen atom or a $C_1$–$C_6$ alkyl group optionally substituted by at least one $C_1$–$C_6$ alkoxycarbonyl;
p is 0 or 1;
$R^{10}$ represents a hydrogen atom or a $C_1$–$C_6$ alkyl group;
$R^{11}$ represents a hydrogen atom, or a $C_1$–$C_6$ alkyl group optionally substituted by at least one substituent selected from carboxyl, $C_1$–$C_6$ alkoxy and $C_1$–$C_6$ alkoxycarbonyl;
$R^{12}$ and $R^{13}$ each independently represent a hydrogen atom, a phenyl group, or a $C_1$–$C_6$ alkyl group optionally substituted by at least one substituent selected from carboxyl and $C_1$–$C_6$ alkoxycarbonyl, or $R^{12}$ and $R^{13}$ together with the nitrogen atom to which they are attached form a 4- to 7-membered saturated heterocycle;
$R^{14}$ and $R^{15}$ each independently represent a hydrogen atom, a phenyl group, a $C_3$–$C_6$ cycloalkyl group, or a $C_1$–$C_6$ alkyl group optionally substituted by at least one substituent selected from carboxyl and $C_1$–$C_6$ alkoxycarbonyl, or $R^{14}$ and $R^{15}$ together with the nitrogen atom to which they are attached form a 4- to 7-membered saturated heterocycle;
$R^{16}$ and $R^{17}$ each independently represent a hydrogen atom, or a $C_1$–$C_6$ alkyl group optionally substituted by at least one substituent selected from carboxyl and $C_1$–$C_6$ alkoxycarbonyl, or $R^{16}$ and $R^{17}$ together with the nitrogen atom to which they are attached form a 4- to 7-membered saturated heterocycle;
$R^{18}$ and $R^{19}$ each independently represent a hydrogen atom, or a $C_1$–$C_6$ alkyl group optionally substituted by at least one substituent selected from carboxyl and $C_1$–$C_6$ alkoxycarbonyl, or $R^{18}$ and $R^{19}$ together with the nitrogen atom to which they are attached form a 4- to 7-membered saturated heterocycle;

$R^{20}$ and $R^{21}$ each independently represent a hydrogen atom, or a $C_1$–$C_6$ alkyl group optionally substituted by at least one substituent selected from carboxyl and $C_1$–$C_6$ alkoxycarbonyl, or $R^{20}$ and $R^{21}$ together with the nitrogen atom to which they are attached form a 4- to 7-membered saturated heterocycle;

$R^{22}$ represents a hydrogen atom, or a $C_1$–$C_6$ alkyl group optionally substituted by at least one substituent selected from carboxyl and $C_1$–$C_6$ alkoxycarbonyl;

$R^{23}$ represents a group $C_1$–$C_6$ alkyl, $C_2$–$C_6$ alkenyl, $C_3$–$C_6$ cycloalkyl, adamantyl, $C_5$–$C_6$ cycloalkenyl, phenyl or a saturated or unsaturated 5- to 10-membered heterocyclic ring system comprising at least one ring heteroatom selected from nitrogen, oxygen and sulphur, each group being optionally substituted by at least one substituent selected from nitro, hydroxyl, oxo, halogen, carboxyl, $C_1$–$C_6$alkyl, $C_1$–$C_6$alkoxy, $C_1$–$C_6$alkylthio, $C_1$–$C_6$ alkylcarbonyl, $C_1$–$C_6$ alkoxycarbonyl, phenyl and —NHC(O)—$R^{24}$; and $R^{24}$ represents a $C_1$–$C_6$ alkyl, amino (—$NH_2$) or phenyl group;

or a pharmaceutically acceptable salt or solvate thereof.

In the context of the present specification, an alkyl substituent group or an alkyl moiety in a substituent group may be linear or branched. A haloalkyl or haloalkoxy substituent group will comprise at least one halogen atom, e.g. one, two, three or four halogen atoms. When $R^6$ and $R^7$, or $R^7$ and $R^{12}$, or $R^{13}$ and $R^{14}$, or $R^{15}$ and $R^{16}$, or $R^{17}$ and $R^{18}$, or $R^{19}$ or $R^{20}$ and $R^{21}$ represent a saturated heterocycle, it should be understood that the only heteroatom present is the nitrogen atom to which $R^6$ and $R^7$, or $R^{12}$ and $R^{13}$, or $R^{14}$ and $R^{15}$, or $R^{16}$ and $R^{17}$, or $R^{18}$ and $R^{19}$, or $R^{20}$ and $R^{21}$ are attached. In the definition of $R^{23}$, it should be noted that the saturated or unsaturated 5- to 10-membered heterocyclic ring system may have alicyclic or aromatic properties.

In one embodiment, the integer m is 1 or 2.

Each $R^1$ independently represents halogen (e.g. chlorine, fluorine, bromine or iodine), cyano, nitro, carboxyl, hydroxyl, $C_3$–$C_6$ cycloalkyl (cyclopropyl, cyclobutyl, cyclopentyl or cyclohexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkoxycarbonyl (e.g. methoxycarbonyl or ethoxycarbonyl), $C_1$–$C_6$, preferably $C_1$–$C_4$, haloalkyl (e.g. trifluoromethyl), $C_1$–$C_6$, preferably $C_1$–$C_4$, haloalkoxy (e.g. trifluoromethoxy), —$NR^6R^7$, $C_3$–$C_6$ cycloalkylamino (e.g. cyclopropylamino, cyclobutylamino, cyclopentylamino or cyclohexylamino), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkylcarbonylamino (e.g. methylcarbonylamino or ethylcarbonylamino), sulphonamido, $C_1$–$C_6$, preferably $C_1$–$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —$C(O)NR^8R^9$, —$NR^{10}C(O)$—$(NH)_pR^{11}$, phenyl, or $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl and $C_1$–$C_6$, preferably $C_1$–$C_4$, alkoxycarbonyl (e.g. methoxycarbonyl or ethoxycarbonyl).

In an embodiment of the invention, each $R^1$ independently represents halogen particularly chlorine or fluorine), cyano, nitro, $C_1$–$C_6$ alkoxy particularly methoxy), $C_1$–$C_6$ alkylcarbonyl particularly methylcarbonyl) or $C_1$–$C_6$ alkylcarbonylamino (particularly methylcarbonylamino). In another embodiment, each $R^1$ represents a halogen atom.

Q preferably represents an oxygen atom.

$R^2$ represents an unsaturated 5- to 10-membered ring system which may comprise at least one ring heteroatom (e.g. one, two or three ring heteroatoms independently) selected from nitrogen, oxygen and sulphur, the ring system being optionally substituted by at least one substituent (e.g. one, two, three or four substituents independently) selected from halogen (e.g. chlorine, fluorine, bromine or iodine), cyano, oxo, nitro, carboxyl, hydroxyl, $C_2$–$C_6$ alkenyl (e.g. ethenyl or 2-propenyl), $C_3$–$C_6$ cycloalkyl (cyclopropyl, cyclobutyl, cyclopentyl or cyclohexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkoxycarbonyl (e.g. methoxycarbonyl or ethoxycarbonyl), $C_1$–$C_6$, preferably $C_1$–$C_4$, haloalkyl (e.g. trifluoromethyl), $C_1$–$C_6$, preferably $C_1$–$C_4$, haloalkoxy (e.g. trifluoromethoxy), —$NR^{12}R^{13}$, $C_3$–$C_6$ cycloalkylamino (e.g. cyclopropylamino, cyclobutylamino, cyclopentylamino or cyclohexylamino), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), phenylcarbonyl, $C_1$–$C_6$, preferably $C_1$–$C_4$, alkylcarbonylamino (e.g. methylcarbonylamino or ethylcarbonylamino), sulphonamido, $C_1$–$C_6$, preferably $C_1$–$C_4$, alkylsulphonyl (e.g. methylsulphonyl, ethylsulphonyl, n-propylsulphonyl, isopropylsulphonyl, n-butylsulphonyl, n-pentylsulphonyl or n-hexylsulphonyl), —$C(O)NR^{14}R^{15}$, $C_1$–$C_6$ alkoxycarbonyl$C_1$–$C_6$ alkyl, preferably $C_1$–$C_4$ alkoxycarbonyl$C_1$–$C_4$ alkyl (e.g. methoxycarbonylmethyl or methoxycarbonylethyl), phenyl, methyltetrazolyl, —$NHSO_2CH_3$, —$NHC(O)NR^{16}R^{17}$, —$OC(O)NR^{18}R^{19}$, —$OCH_2C(O)NR^{20}R^{21}$, —$NHC(O)OR^{22}$, —$NHC(O)R^{23}$, and $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) itself optionally substituted by at least one (e.g. one or two substituents independently) selected from carboxyl and $C_1$–$C_6$, preferably $C_1$–$C_4$, alkoxycarbonyl (e.g. methoxycarbonyl or ethoxycarbonyl).

The unsaturated 5- to 10-membered ring system in $R^2$ may be monocyclic or polycyclic (fused or otherwise), e.g. bicyclic, examples of which include phenyl, naphthyl, 1,3-benzodioxolyl, pyrazolyl, thienyl, oxazolyl, imidazolyl, pyridinyl, pyridopyrrolyl, benzimidazolyl, indazolyl, benzothiazolyl, quinolinyl, tetrahydroquinolinyl (e.g. 1,2,3,4-tetrahydroquinolinyl), thiazolyl and benzotriazolyl. For example, the unsaturated 5- to 10-membered ring system in $R^2$ may be selected from the group consisting of phenyl, 1,3-benzodioxolyl, naphthyl, benzothiazolyl, benzoxazolyl, benzisoxazolyl and tetrahydroquinolinyl. Alternatively, the ring system in $R^2$ is monocyclic and 5- or 6-membered, especially phenyl.

In one embodiment, the unsaturated 5- to 10-membered ring system in $R^2$ is optionally substituted by at least one substituent selected from halogen, cyano, oxo, $C_1$–$C_6$ alkyl, $C_2$–$C_6$ alkenyl, $C_1$–$C_6$ alkoxy, —$NR^{12}R^{13}$, $C_1$–$C_6$ alkylcarbonyl, phenylcarbonyl, methyltetrazolyl, —$C(O)NR^{14}R^{15}$, —$NHC(O)NR^{16}R^{17}$ and —$NHC(O)R^{23}$.

Each $R^3$ independently represents a $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), $C_1$–$C_6$, preferably $C_1$–$C_4$, alkoxycarbonyl (e.g. methoxycarbonyl or ethoxycarbonyl), —$CH_2OH$ or carboxyl group. In one embodiment, each $R^3$ independently represents a methyl, methoxycarbonyl, ethoxycarbonyl, —$CH_2OH$ or carboxyl group.

$R^4$ and $R^5$ each independently represent a hydrogen atom or a $C_1$–$C_6$, preferably $C_1$–$C_4$, alkyl (e.g. methyl, ethyl, n-propyl, isopropyl, n-butyl, isobutyl, tert-butyl, n-pentyl or n-hexyl) group.

$R^6$ and $R^7$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl), or $R^6$ and $R^7$ together with the nitrogen atom to which they are attached form a 4 to 7-membered saturated heterocycle (such as pyrrolidinyl or piperidinyl).

$R^8$ and $R^9$ each independently represent a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one (e.g. one or two) $C_1$–$C_6$, preferably $C_1$–$C_4$, alkoxycarbonyl.

$R^{10}$ represents a hydrogen atom or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl).

$R^{11}$ represents a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl, $C_1$–$C_6$, preferably $C_1$–$C_4$, alkoxy and $C_1$–$C_6$, preferably $C_1$–$C_4$, alkoxycarbonyl.

$R^{12}$ and $R^{13}$ each independently represent a hydrogen atom, a phenyl group, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl and $C_1$–$C_6$, preferably $C_1$–$C_4$, alkoxycarbonyl (e.g. methoxycarbonyl or ethoxycarbonyl), or $R^{12}$ and $R^{13}$ together with the nitrogen atom to which they are attached form a 4- to 7-membered saturated heterocycle (such as pyrrolidinyl or piperidinyl).

$R^{14}$ and $R^{15}$ each independently represent a hydrogen atom, a phenyl group, a $C_3$–$C_6$ cycloalkyl (cyclopropyl, cyclobutyl, cyclopentyl or cyclohexyl) group, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl and $C_1$–$C_6$, preferably $C_1$–$C_4$, alkoxycarbonyl (e.g. methoxycarbonyl or ethoxycarbonyl), or $R^{14}$ and $R^{15}$ together with the nitrogen atom to which they are attached form a 4- to 7-membered saturated heterocycle (such as pyrrolidinyl or piperidinyl).

$R^{16}$ and $R^{17}$ each independently represent a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl and $C_1$–$C_6$, preferably $C_1$–$C_4$, alkoxycarbonyl (e.g. methoxycarbonyl or ethoxycarbonyl), or $R^{16}$ and $R^{17}$ together with the nitrogen atom to which they are attached form a 4- to 7-membered saturated heterocycle (such as pyrrolidinyl or piperidinyl).

$R^{18}$ and $R^{19}$ each independently represent a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl and $C_1$–$C_6$, preferably $C_1$–$C_4$, alkoxycarbonyl (e.g. methoxycarbonyl or ethoxycarbonyl), or $R^{18}$ and $R^{19}$ together with the nitrogen atom to which they are attached form a 4- to 7-membered saturated heterocycle (such as pyrrolidinyl or piperidinyl).

$R^{20}$ and $R^{21}$ each independently represent a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl and $C_1$–$C_6$, preferably $C_1$–$C_4$, alkoxycarbonyl (e.g. methoxycarbonyl or ethoxycarbonyl), or $R^{20}$ and $R^{21}$ together with the nitrogen atom to which they are attached form a 4- to 7-membered saturated heterocycle (such as pyrrolidinyl or piperidinyl).

$R^{22}$ represents a hydrogen atom, or a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl) optionally substituted by at least one substituent (e.g. one or two substituents independently) selected from carboxyl and $C_1$–$C_6$, preferably $C_1$–$C_4$, alkoxycarbonyl (e.g. methoxycarbonyl or ethoxycarbonyl).

$R^{23}$ represents a group $C_1$–$C_6$, preferably $C_1$–$C_5$, alkyl group (e.g. methyl, ethyl, n-propyl, isopropyl, n-butyl, isobutyl, tert-butyl, n-pentyl or n-hexyl), $C_2$–$C_6$, preferably $C_2$–$C_4$, alkenyl, $C_3$–$C_6$ cycloalkyl (cyclopropyl, cyclobutyl, cyclopentyl or cyclohexyl), adamantyl, $C_5$–$C_6$ cycloalkenyl, phenyl or a saturated or unsaturated 5- to 10-membered heterocyclic ring system comprising at least one heteroatom (e.g. one, two, three or four heteroatoms independently) selected from nitrogen, oxygen and sulphur, each group being optionally substituted by at least one substituent (e.g. one, two, three or four substituents independently) selected from nitro, hydroxyl, oxo, halogen (e.g. fluorine, chlorine, bromine or iodine), carboxyl, $C_1$–$C_6$, preferably $C_1$–$C_4$, alkyl (e.g. methyl, ethyl, n-propyl, isopropyl, n-butyl, isobutyl, tert-butyl, n-pentyl or n-hexyl), $C_1$–$C_6$, preferably $C_1$–$C_4$, alkoxy (e.g. methoxy, ethoxy, n-propoxy or n-butoxy), $C_1$–$C_6$, preferably $C_1$–$C_4$, alkylthio (e.g. methylthio or ethylthio), $C_1$–$C_6$, preferably $C_1$–$C_4$, alkylcarbonyl (e.g. methylcarbonyl, ethylcarbonyl, n-propylcarbonyl, isopropylcarbonyl, n-butylcarbonyl, n-pentylcarbonyl or n-hexylcarbonyl), $C_1$–$C_6$, preferably $C_1$–$C_4$, alkoxycarbonyl (e.g. methoxycarbonyl or ethoxycarbonyl), phenyl and —NHC(O)—$R^{24}$.

The saturated or unsaturated 5- to 10-membered heterocyclic ring system may be monocyclic or polycyclic (fused or otherwise), e.g. bicyclic, and may comprise up to four heteroatoms independently selected from nitrogen, oxygen and sulphur. Examples of ring systems that may be used include pyrrolidinyl, piperidinyl, pyrazolyl, thiazolidinyl, thienyl, isoxazolyl, thiadiazolyl, pyrrolyl, furanyl, thiazolyl, indolyl, quinolinyl, benzimidazolyl, triazolyl, tetrazolyl and pyridinyl.

$R^{24}$ represents a $C_1$–$C_6$, preferably $C_1$–$C_4$, alkyl group (e.g. methyl, ethyl, n-propyl, isopropyl, n-butyl, isobutyl, tert-butyl, n-pentyl or n-hexyl), amino or phenyl group.

In an embodiment of the invention, m is 1;
$R^1$ represents halogen;
$Z^1$ represents $CH_2$;
$Z^2$ represents $CH_2$;
Q represents an oxygen atom;
$R^2$ represents an unsaturated 5- to 10-membered ring system comprising from 0 to 2 ring heteroatoms selected from nitrogen, oxygen and sulphur, the ring system being optionally substituted by at least one substituent (e.g. from 1 to 3 substituents) independently selected from halogen, cyano, oxo, $C_1$–$C_6$ alkyl, $C_2$–$C_6$ alkenyl, $C_1$–$C_6$ alkoxy, —$NR^{12}R^{13}$, $C_1$–$C_6$ alkylcarbonyl, phenylcarbonyl, —$C(O)NR^{14}R^{15}$, methyltetrazolyl, —$NHC(O)NR^{16}R^{17}$ and —$NHC(O)R^{23}$;

n is 0;

$R^4$ and $R^5$ each represent a hydrogen atom;

$R^{12}$ and $R^{13}$ each independently represent a hydrogen atom or a phenyl group;

$R^{14}$ and $R^{15}$ each independently represent a hydrogen atom, a phenyl group, a $C_3$–$C_6$ cycloalkyl group or a $C_1$–$C_6$ alkyl group;

$R^{16}$ and $R^{17}$ each independently represent a hydrogen atom or a $C_1$–$C_6$ alkyl group; and $R^{23}$ represents a $C_1$–$C_6$ alkyl group or a phenyl group.

Examples of compounds of the invention include:

N-[2-({4-[1-(4-Chlorobenzyl)-4-piperidinyl]-2-morpholinyl}methoxy)-phenyl]acetamide,
1-[3-({4-[1-(4-Chlorobenzyl)-4-piperidinyl]-2-morpholinyl}methoxy)phenyl]-1-ethanone,
2-[(1,3-Benzodioxol-5-yloxy)methyl]-4-[1-(4-chlorobenzyl)-4-piperidinyl]morpholine,
4-[1-(4-Chlorobenzyl)-4-piperidinyl]-2-[(2-naphthyloxy)methyl]morpholine,
4-[1-(4-Chlorobenzyl)-4-piperidinyl]-2-[(3-methoxyphenoxy)methyl]morpholine,
3-({4-[1-(4-Chlorobenzyl)-4-piperidinyl]-2-morpholinyl}methoxy)benzonitrile,
4-[1-(4-Chlorobenzyl)-4-piperidinyl]-2-[3,4-difluorophenoxy)methyl]morpholine,
4-[1-(4-Chlorobenzyl)-4-piperidinyl]-2-[(2-ethoxyphenoxy)methyl]morpholine,
4-[1-(4-Chlorobenzyl)-4-piperidinyl]-2-[(2-chlorophenoxy)methyl]morpholine,
N-[2-({(2S)-4-[1-(4-Chlorobenzyl)-4-piperidinyl]morpholinyl}methoxy)phenyl]-acetamide,
N-[2-({(2R)-4-[1-(4-Chlorobenzyl)-4-piperidinyl]morpholinyl}methoxy)phenyl]-acetamide,
N-[2{4-[1-(4-Chlorobenzyl)-4-piperidinyl]-2-morpholinyl}methoxy)phenyl]-benzamide,
2-({4-[1-(4-Chlorobenzyl)-4-piperidinyl]-2-morpholinyl}methoxy)-N-phenyl-benzamide,
2-({4-[1-(4-Chlorobenzyl)-4-piperidinyl]-2-morpholinyl}methoxy)-N-methyl-benzamide,
2-[1-(4-Chlorobenzyl)-4-piperidinyl]-2-[(1-naphthyloxy)methyl]morpholine,
2-({4-[1-(4-Chlorobenzyl)-4-piperidinyl]-2-morpholinyl}methoxy)-1,3-benzothiazole,
[3-({4-[1-(4-Chlorobenzyl)-4-piperidinyl]-2-morpholinyl}methoxy)-phenyl]-(phenyl)methanone,
4-[1-(4-Chlorobenzyl)-4-piperidinyl]-2-({2-[(E)-1-propenyl]phenoxy}-methyl)-morpholine,
2-({4-[1-(4-Chlorobenzyl)-4-piperidinyl]-2-morpholinyl}methoxy)-N-cyclopropyl-benzamide,
4-[1-(4-Chlorobenzyl)-4-piperidinyl]-2-[(2-iodophenoxy)methyl]morpholine,
4-[1-(4-Chlorobenzyl)-4-piperidinyl]-2-[(4-chloro-2-isopropyl-5-methylphenoxy)-methyl]morpholine,
4-({4-[1-(4-Chlorobenzyl)-4-piperidinyl]-2-morpholinyl}methoxy)-2-methyl-1,3-benzoxazole,
4-[1-(4-Chlorobenzyl)-4-piperidinyl]-2-[(2,4-dichlorophenoxy)methyl]morpholine,
N-[2-({4-[1-(4-Chlorobenzyl)-4-piperidinyl]-2-morpholinyl}methoxy)phenyl]urea,
N-[2-({4-[1-(4-Chlorobenzyl)-4-piperidinyl]-2-morpholinyl}methoxy)phenyl]-N'-ethylurea,
N'-[2-({4-[1-(4-Chlorobenzyl)-4-piperidinyl]-2-morpholinyl}methoxy)phenyl]-N,N-dimethylurea,
8-({4-[1-(4-Chlorobenzyl)-4-piperidinyl]-2-morpholinyl}methoxy)-3,4-dihydro-2(1H)-quinoline,
N-Benzyl-2-({4-[1-(4-chlorobenzyl)-4-piperidinyl]-2-morpholinyl}methoxy)aniline,
4-({4[1-(4-Chlorobenzyl)-4-piperidinyl]-2-morpholinyl}methoxy)-2-methyl-1,3-benzoxazole,
4-[1-(4-Chlorobenzyl)-4-piperidinyl]-2-{[2-(2-methyl)-2H-1,2,3,4-tetrazol-5-yl)phenoxy]methyl}morpholine,
4-[1-(4-Chlorobenzyl)-4-piperidinyl]-2-[(3,5-difluorophenyl)methyl]morpholine, and pharmaceutically acceptable salts and solvates of any one thereof.

The present invention further provides a process for the preparation of a compound of formula (I) as defined above which comprises (i) when Q represents an oxygen or sulphur atom or a group NH, reacting a compound of general formula

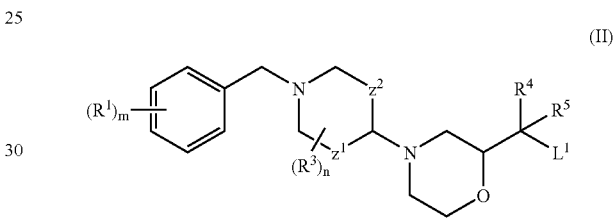

(II)

wherein $L^1$ represents a leaving group (e.g. nitrobenzenesulphonate) and m, n, $Z^1$, $Z^2$, $R^1$, $R^3$, $R^4$ and $R^5$ are as defined in formula (I), with a compound of general formula $$R^2\text{-Q'H} \qquad (III)$$

wherein Q' represents an oxygen or sulphur atom or a group NH and $R^2$ is as defined in formula (I); or (ii) when Q represents a group $CH_2$, reacting a compound of general formula $$R^2\text{—}CH_2\text{-}L^2 \qquad (IV)$$

wherein $L^2$ represents a halogen atom and $R^2$ is as defined in formula (I), with an alkali metal (e.g. lithium or sodium), followed by reaction with a compound of formula (II) as defined in (i) above;

and optionally after (i) or (ii) forming a pharmaceutically acceptable salt or solvate of the compound of formula (I) obtained.

Compounds of formula (II) in which, for example, $R^4$ and $R^5$ both represent hydrogen may conveniently be prepared according to the following reaction scheme:

(A)

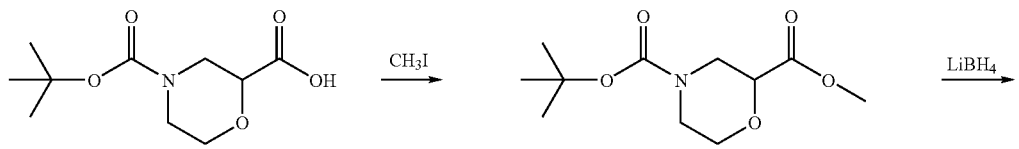

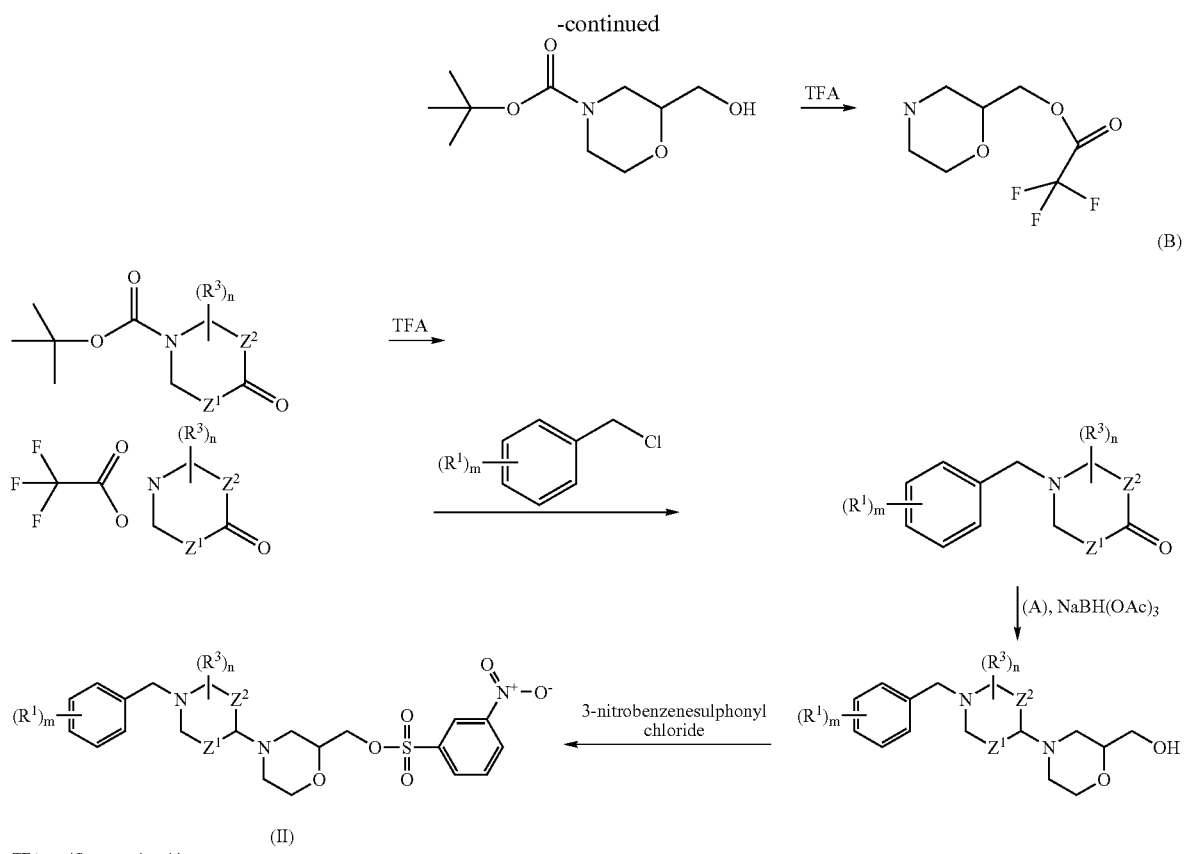

TFA = trifluoroacetic acid

Other compounds of formula (II) and compounds of formulae (III) and (IV) are either commercially available, are well known in the literature or may be prepared easily using known techniques.

It will be appreciated by those skilled in the art that in the process of the present invention certain functional groups such as hydroxyl or amino groups in the starting reagents or intermediate compounds may need to be protected by protecting groups. Thus, the preparation of the compounds of formula (I) may involve, at an appropriate stage, the removal of one or more protecting groups.

The protection and deprotection of functional groups is described in 'Protective Groups in Organic Chemistry', edited by J. W. F. McOmie, Plenum Press (1973) and 'Protective Groups in Organic Synthesis', 2nd edition, T. W. Greene and P. G. M. Wuts, Wiley-Interscience (1991).

The compounds of formula (I) above may be converted to a pharmaceutically acceptable salt or solvate thereof, preferably an acid addition salt such as a hydrochloride, hydrobromide, phosphate, acetate, fumarate, maleate, tartrate, citrate, oxalate, methanesulphonate or p-toluenesulphonate.

Compounds of formula (I) are capable of existing in stereoisomeric forms. It will be understood that the invention encompasses the use of all geometric and optical isomers (including atropisomers) of the compounds of formula (I) and mixtures thereof including racemates. The use of tautomers and mixtures thereof also form an aspect of the present invention. Enantiomerically pure forms are particularly desired.

The compounds of formula (I) have activity as pharmaceuticals, in particular as modulators of chemokine receptor (especially MIP-1α chemokine receptor) activity, and may be used in the treatment of autoimmune, inflammatory, proliferative and hyperproliferative diseases and immunologically-mediated diseases including rejection of transplanted organs or tissues and Acquired Immunodeficiency Syndrome (AIDS).

Examples of these conditions are:

(1) (the respiratory tract) airways diseases including chronic obstructive pulmonary disease (COPD) such as irreversible COPD; asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjögren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia greata and vernal conjunctivitis;

(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;

(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;

(6) (allograft rejection) acute and chronic following, for example, transplantation of kidney, heart, liver, lung, bone marrow, skin and cornea; and chronic graft versus host disease;

(7) cancers, especially non-small cell lung cancer (NSCLC) and squamous sarcoma;

(8) diseases in which angiogenesis is associated with raised chemokine levels; and (9) cystic fibrosis, stroke, re-perfusion injury in the heart, brain, peripheral limbs and sepsis.

Thus, the present invention provides a compound of formula (I), or a pharmaceutically-acceptable salt or solvate thereof, as hereinbefore defined for use in therapy.

In a further aspect, the present invention provides the use of a compound of formula (I), or a pharmaceutically acceptable salt or solvate thereof, as hereinbefore defined in the manufacture of a medicament for use in therapy.

In the context of the present specification, the term "therapy" also includes "prophylaxis" unless there are specific indications to the contrary. The terns "therapeutic" and "therapeutically" should be construed accordingly.

The invention also provides a method of treating an inflammatory disease which comprises administering to a patient in need thereof a therapeutically effective amount of a compound of formula (I), or a pharmaceutically acceptable salt or solvate thereof, as hereinbefore defined.

The invention still further provides a method of treating an airways disease which comprises administering to a patient in need thereof a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of administration, the treatment desired and the disorder indicated. The daily dosage of the compound of formula (I) may be in the range from 0.001 mg/kg to 30 mg/kg.

The compounds of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the skin or to the lung and/or airways) in the form, e.g., of creams, solutions, suspensions, heptafluoroalkane aerosols and dry powder formulations; or systemically, e.g. by oral administration in the form of tablets, capsules, syrups, powders or granules; or by parenteral administration in the form of solutions or suspensions; or by subcutaneous administration; or by rectal administration in the form of suppositories; or transdermally.

The invention will now be further explained by reference to the following illustrative examples, in which $^1$H NMR spectra were recorded on Varian Unity Inova 400. The central solvent peak of chloroform-d ($\delta_H$ 7.27 ppm) were used as internal standard. Low resolution mass spectra and accurate mass determination were recorded on a Hewlett-Packard 1100 LC-MS system equipped with APCI/ESI ionisation chambers. All solvents and commercial reagents were laboratory grade and used as received. The nomenclature used for the compounds was generated with ACD/IUPAC Name Pro.

EXAMPLE-1

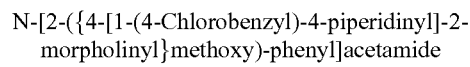

N-[2-({4-[1-(4-Chlorobenzyl)-4-piperidinyl]-2-morpholinyl}methoxy)-phenyl]acetamide (i) 4-(tert-Butyl) 2-methyl 2,4-morpholinedicarboxylate Methyl iodide (9.38 ml, 150 mmol) was added to a suspension of 4-(tert-butoxycarbonyl)-2-morpholinecarboxylic acid (14.5 g, 62.6 mmol) and dry potassium carbonate (17.3 g, 125 mmol) in dry dimethylformamide (DMF) (360 ml). The mixture was stirred over night, filtered through Celite and concentrated. The residue was partitioned between dichloromethane and water. The organic phase was dried over magnesium sulfate and concentrated to give 22 g of crude product.

$^1$H-NMR (400 MHz, CDCl$_3$): δ 4.07 (2H, dd), 3.99 (1H, 2m), 3.77 (3H, s), 3,73 (1H, m), 3.55 (1H, m), 3.07 (2H, m), 1.45 (9H, s).

(ii) tert-Butyl 2(hydroxymethyl)-4-morpholinecarboxylate

The crude product from step (i) (62.6 mmol) was dissolved in dry tetrahydrofuran (THF) (100 ml) and added dropwise at 0° C. to a suspension of lithium borohydride (2.50 g, 115 mmol) in dry THF (100 ml). The mixture was allowed to attain room temperature over night. Water (10 ml) was added and after stirring for 1 h the mixture was concentrated. The residue was partitioned between ethyl acetate and water. The organic phase was washed with 0.5 M hydrochloric acid, saturated sodium hydrogen carbonate and water. Drying over magnesium sulfate and concentration gave the title compound as a crude product (13.3 g).

$^1$H-NMR (400 MHz, CDCl$_3$): δ 3.88 (3H, m), 3.46–3.72 (4H, m), 2.93 (1H, m), 2.75 (1H, m), 2.09 (1H, m), 1.46 (9H, s).

(iii) 2-Morpholinylmethyl 2,2,2 trifluoroacetate (trifluoroacetic acid salt)

Tert-butyl 2-(hydroxymethyl)-4-morpholinecarboxylate, obtained from step (ii) (5.13 g, 23.61 mmol) was treated with trifluoroacetic acid (20 mL) in dichloromethane (50 mL) at room temperature for 3 h. The volatiles were removed in vacuo to give subtitled compound (yield 7.6 g).

$^1$H-NMR (DMSOd$_6$, 400 MHz): δ 9.25 (br.,s, 2H); 3.86 (dd, J=3.3, 12.6 Hz, 1H); 3.62 (m, 2H); 3.39 (m, 2H); 3.19 (m, 2H); 2.96 (t, J=11.2 Hz, 1H); 2.76 (t,J=11.2 Hz, 1H).

(iv) 1,4-Piperidinone trifluoroacetate

To a solution of tert-butyl 4-oxo-1-piperidinecarboxylate (797 mg, 4.0 mmol) in dichloromethane (CH$_2$Cl$_2$) (10 mL) was added trifluoroacetic acid (5 mL) and the reaction mixture was kept at room temperature for 90 min. The volatiles were removed in vacuo to give subtitled compound (853 mg) which was directly used in the next step.

(v) 1-(4-Chlorobenzyl)-4-piperidinone

To a solution of 4-piperidine trifluoroacetate obtained from step (iv) (853 mg, 4.0 mmol) in DMF was added triethylamine (2.66 mL, 19.2 mmol), followed by 4-chlorobenzyl chloride (753 mg, 4.8 mmol) and the reaction mixture was stirred overnight at room temperature. The volatiles were removed in vacuo, residue was dissolved in ethylacetate, washed with water (H$_2$O), organic layer was dried over sodium sulphate (Na$_2$SO$_4$), filtered and concentrated. The residue was purified by silica gel flash chromatography to give the subtitled compound (350 mg).

$^1$H-NMR (CDCl$_3$, 400 MHz): δ 7.37 (s, 4H); 3.6 (s, 2H); 2.78 (s, 4H); 2.42 (s, 4H).

(vi) {4-[1-(4-Chlorophenyl)-4-piperidinyl]-2-morpholinyl}methanol

To a mixture of 1-(4-chlorobenzyl)-4-piperidinone obtained from step (v) (953 mg, 4.26 mmol), 2-morpholinylmethyl 2,2,2 trifluoroacetate (trifluoroacetic acid salt) obtained from step (iii) (700 mg, 2.13 mmol) in methanol (10 mL) was added half portion of sodium triacetoxyborohydride (NaBH(OAc)$_3$) (1.80 mg, 8.52 mmol) and the reaction mixture kept on stirring at room temperature for 5 h then another portion of NaBH(OAc)$_3$ (4.26 mmol) was added and the reaction mixture kept on stirring at room temperature overnight. The volatiles were removed in vacuo, residue dissolved in chloroform, washed successively with saturated aqueous sodium hydrogen carbonate (NaHCO$_3$) and water (H$_2$O). The organic layer was dried over sodium sulphate (Na$_2$SO$_4$), filtered, concentrated and the residue was purified by silica gel flash chromatography to give the subtitled compound (125 mg).

$^1$H-NMR (CDCl$_3$, 300 MHz): δ 7.25 (m, 4H); 3.90 (m, 1H); 3.72–3.50 (m, 4H); 3.41 (s, 2H); 2.94–2.62 (m, 5H); 2.38–2.08 (m, 3H); 1.95 (br. t, J=10.4 Hz, 2H); 1.78 (br. D, J=12.4 Hz, 2H); 1.52 (m, 2H). APCI-MS: m/z 325 (MH$^+$).

(vii) {4-[1-(4-Chlorophenyl)-4-piperidinyl]-2-morpholinyl}methyl-3-nitrobenzenesulfonate To a solution of {4-[1-(4-chlorophenyl)-4-piperidinyl]-2-morpholinyl}methanol obtained from step (vi) (125 mg, 0.384 mmol) in dichloromethane (CH$_2$Cl$_2$) (2 mL) was added triethylamine (0.240 mL, 1.72 mmol) followed by 3-nitrobenzenesulfonyl chloride (127.5 mg, 0.575 mmol) and the reaction mixture kept on stirring at room temperature overnight. The volatiles were removed in vacuo, residue dissolved in chloroform, washed sucessively with saturated aqueous sodium hydrogen carbonate (NaHCO$_3$) and water (H$_2$O). The organic layer was dried over sodium sulphate (Na$_2$SO$_4$), filtered, concentrated and the residue was purified by silica gel flash chromatography to give the subtitled compound (163 mg).

$^1$H-NMR (CDCl$_3$, 300 MHz): δ 8.78 (m, 1H); 8.50 (m, 1H); 8.24 (m, 1H); 7.78 (t, J=8.0 Hz, 1H); 7.24 (m, 4H); 4.18 (d, J=4.8 Hz, 2H); 3.75 (m, 2H); 3.50 (m, 3H); 2.92 (br, D J=8.0 Hz, 2H); 2.75 (d, J=10.8 Hz, 1H); 2.62 (d, J=11.5 Hz, 1H); 2.32–1.90 (m, 5H) 1.72 (m, 2H); 1.50 (m, 2H). APCI-MS: m/z 510 (MH$^+$).

(viii) N-[2-({4-[1-(4-Chlorobenzyl)-4-piperidinyl]-2-morpholinyl}methoxy)phenyl]-acetamide A mixture of {4-[1-(4-chlorophenyl)-4-piperidinyl]-2-morpholinyl}methyl-3-nitrobenzenesulfonate obtained from step (vii) (137 mg, 0.268 mmol), 2-acetamidophenol (60.8 mg, 0.402 mmol) and potassium carbonate (K$_2$CO$_3$) (350 mg) in DMF (3 mL) was kept on stirring at 65° C. for 4 h. The reaction mixture was cooled down to room temperature and partitioned between ethylacetate and water. The organic layer was dried over sodium sulphate (Na$_2$SO$_4$), filtered and concentrated. The residue was purified by silica gel flash chromatography to give the titled compound (72 mg).

$^1$H-NMR (CDCl$_3$, 300 MHz): δ 8.35 (m, 1H); 8.15 (br. S, 1H); 7.30 (br. S, 4H); 7.00 (m, 2H); 6.91 (m, 1H); 4.04–3.86 (m, 4H); 3.74 (t, J=11.1 Hz, 1H); 3.52 (br. S, 2H); 2.96 (br. D, J=8.4 Hz, 2H); 2.84 (d, J=11.0 Hz, 1H); 2.77 (d, J=11.4 Hz, 1H); 2.45–2-23 (m, 3H); 2.18 (s, 3H); 2.08 (br. s, 2H); 1.80 (br. S, 2H); 1.64 (br. S, 2H). APCI-MS: m/z 458 (MH$^+$).

The compounds of Examples 2 to 31 were prepared by processes similar to that described in Example 1.

EXAMPLE-2

1-[3-({4-[1-(4-Chlorobenzyl)-4-piperidinyl]-2-morpholinyl}methoxy)phenyl]-1-ethanone APCI-MS: m/z 443 (MH$^+$).

EXAMPLE-3

2-[(1,3-Benzodioxol-5-yloxy)methyl]4-[1-(4-chlorobenzyl)-4-piperidinyl]morpholine APCI-MS: m/z 445 (MH$^+$).

EXAMPLE-4

4-[1-(4-Chlorobenzyl)-4-piperidinyl]-2-[(2-naphthyloxy)methyl]morpholine

APCI-MS: m/z 451 (MH$^+$).

EXAMPLE-5

4-[1-(4-Chlorobenzyl)-4-piperidinyl]-2-[(3-methoxyphenoxy)methyl]morpholine

APCI-MS: m/z 431 (MH$^+$).

EXAMPLE-6

3-({4-[1-(4-Chlorobenzyl)-4-piperidinyl]-2-morpholinyl}methoxy)benzonitrile

APCI-MS: m/z 426 (MH$^+$).

EXAMPLE-7

4-[1-(4-Chlorobenzyl)-4-piperidinyl]-2-[3,4-difluorophenoxy)methyl]morpholine

APCI-MS: m/z 437 (MH$^+$).

EXAMPLE-8

4-[1-(4-Chlorobenzyl)-4-piperidinyl]-2-[(2-ethoxyphenoxy)methyl]morpholine

APCI-MS: m/z 445 (MH$^+$).

EXAMPLE-9

4-[1-(4-Chlorobenzyl)-4-piperidinyl]-2-[(2-chlorophenoxy)methyl]morpholine

APCI-MS: m/z 435 (MH$^+$).

EXAMPLE-10

N-[2-({(2S)-4-[1-(4-Chlorobenzyl)-4-piperidinyl]morpholinyl}methoxy)phenyl]-acetamide APCI-MS: m/z 458 (MH$^+$). $^1$H-NMR (CDCl$_3$, 400 MHz): δ 8.36 (m, 1H); 8.17 (br.,s, 1H); 7.27 (m, 4H); 7.00 (m, 2H); 6.92 (m, 4H); 4.05–3.89 (m, 4H); 3.77 (m, 1H); 3.49 (s, 2H); 2.98 (d, J=11.7 Hz, 1H); 2.81 (m, 2H); 2.48–2.22 (m, 3H); 2.18 (s, 3H); 2.05 (br.,s, 2H); 1.81 (br.d, J=11.4 Hz, 2H); 1.62 (br.m, 2H).

EXAMPLE-11

N-[2-({(2R)-4-[14-Chlorobenzyl)-4-piperidinyl]morpholinyl}methoxy)phenyl]-acetamide APCI-MS: m/z 458 (MH$^+$).

EXAMPLE-12

N-[2{4-[1-(4-Chlorobenzyl)-4-piperidinyl]-2-morpholinyl}methoxy)phenyl]-benzamide (i) N-(2-Hydroxyphenyl)benzamide To a mixture of 2-aminophenol (1.09 g, 10.0 mmol) and triethylamine (2.09 mL, 15.0 mmol) in THF (20 mL) was added benzoyl chloride (1.16 mL, 10.0 mmol) in THF (4 mL) dropwise over a period of 5 min at 0° C. After addition was complete the reaction mixture was kept on stirring at room temperature for overnight. The reaction mixture was concentrated at reduced pressure. The residue was taken up in methanol, aqueous sodium hydroxide (NaOH) (8M, 5 mL) was added. After 5 min the pH of the reaction mixture was adjusted to 7.0 by addition of glacial acetic acid and concentrated in vacuo. The reaction mixture was dissolved in dichloromethane (CH$_2$Cl$_2$), washed successively with 1M aqueous hydrochloric acid (HCl), saturated aqueous sodium hydrogen carbonate (NaHCO$_3$). The organic layer was dried over sodium sulphate (Na$_2$SO$_4$), filtered and concentrated to give desired product (1.69 g).

$^1$H-NMR (DMSO-d$_6$, 400 MHz): δ, 9.80 (s, 1H); 9.58 (s, 1H); 8.00 (m, 2H); 7.70 (m, 1H); 7.60 (m, 1H); 7.58 (m, 3H); 7.08 (m, 1H); 6.90 (m, 1H); 6.84 (m, 1H).

(ii) N-[2{4-[1-(4-Chlorobenzyl)-4-piperidinyl]-2-morpholinyl}methoxy)phenyl]benzamide
APCI-MS: m/z 520 (MH$^+$).

EXAMPLE-13

2{4-[1-(4-Chlorobenzyl)-4-piperidinyl]-2-morpholinyl}methoxy)-N-phenyl-benzamide APCI-MS: m/z 520 (MH$^+$).

EXAMPLE-14

2-({4-[1-(4-Chlorobenzyl)-4-piperidinyl]-2-morpholinyl}methoxy)-N-methyl-benzamide (i) 3-Hydroxy-N-methylbenzamide A mixture of 3-hydroxybenzoic acid (1.3 g, 9.4 mmol) and a ethanolic methylamine solution (33%, 1.5 ml, 12.1 mmol) were stirred at 60° C. for 48 h, then the solvent was evaporated in vacuo, and the residue redissolved in a small volume of ethanol. The product precipitated from the solution by the addition of ethyl acetate. The precipitate was collected by filtration and dried to give the subtitled compound (1.3 g, 91%).

$^1$H-NMR (400 MHz, DMSO-d$_6$): δ 7.32 (m, 1H), 7.29 (d, 1H, J=7.6), 7.09 (t, 1H, J=7.6), 6.73 (dm, 1H, J=7.6), 2.37 (s, 3H).

(ii) 2-({4-[1-(4-Chlorobenzyl)-4-piperidinyl]-2-morpholinyl}methoxy)-N-methyl-benzamide
APCI-MS: m/z 458 (MH$^+$).

EXAMPLE-15

2-[1-(4-Chlorobenzyl)-4-piperidinyl]-2-[(1-naphthyloxy)methyl]morpholine

APCI-MS: m/z 451 (MH$^+$).

EXAMPLE-16

2-({4-[1-(4-Chlorobenzyl)-4-piperidinyl]-2-morpholinyl}methoxy)-1,3-benzothiazole APCI-MS: m/z 458 (MH$^+$).

EXAMPLE-17

[3-({4-[1-(4-Chlorobenzyl)-4-piperidinyl]-2-morpholinyl}methoxy)-phenyl]-(phenyl)methanone APCI-MS: m/z 505 (MH$^+$).

EXAMPLE-18

4-[1-(4-Chlorobenzyl)-4-piperidinyl]-2-({2-[(E)-1-propenyl]phenoxy}-methyl)-morpholine APCI-MS: m/z 441 (MH$^+$).

EXAMPLE-19

2-({4-[1-4-Chlorobenzyl)-4-piperidinyl]-2-morpholinyl}methoxy)-N-cyclopropyl-benzamide (i) N-Cyclopropyl-2-hydroxybenzamide A mixture of methylsalicylate (4.36 g, 28.69 mmol) and cyclopropylamine (1.64 g, 28.69 mmol) was heated at 80–100° C. for 3 h. An additional 0.5 equivalent of cyclopropylamine was added and the reaction mixture was kept at 70° C. for overnight. The reaction mixture was co-evaporated with toluene and the residue was purified by silica gel flash chromatography to give the subtitle compound (2.71 g).

$^1$H-NMR (CDCl$_3$, 400 MHz): δ 12.36 (s, 1H); 7.40 (m, 1H); 7.31 (m, 1H); 7.00 (dd, J=0.9 Hz, 8.4 Hz); 6.83 (m, 1H); 6.53 (br.s, 1H); 2.89 (m, 1H); 0.93 (m, 2H); 0.67 (m, 2H).

(ii) 2-({4-[1-(4-Chlorobenzyl)-4-piperidinyl]-2-morpholinyl}methoxy)-N-cyclopropyl-benzamide APCI-MS: m/z 484 (MH$^+$).

EXAMPLE-20

4-[1-(4-Chlorobenzyl)-4-piperidinyl]-2-[(2-iodophenoxy)methyl]morpholine

APCI-MS: m/z 527 (MH$^+$).

EXAMPLE-21

4-[1-(4-Chlorobenzyl)-4-piperidinyl]-2-[(4-chloro-2-isopropyl-5-methylphenoxy)-methyl]morpholine APCI-MS: m/z 491 (MH$^+$).

EXAMPLE-22

4-({4-[1-(4-Chlorobenzyl)-4-piperidinyl]-2-morpholinyl}methoxy)-2-methyl-1,3-benzoxazole (i) 2-Methyl-1,3-benzoxazol-4-ol A solution of 2,6-dihydroxyacetophenone (1.43 g, 9.4 mmol), hydroxylamine hydrochloride (940 mg, 13.6 mmol), potassium hydroxide (KOH) (1.15 g, 20.6 mmol), and water (10 mL) in methanol (15 mL) was heated at reflux temperature under nitrogen for 18 h. The reaction mixture was cooled to room temperature and concentrated in vacuo. The residue was partitioned between ethylacetate and water. The organic layer was extracted with 1H hydrochloric acid (HCl), dried over sodium sulphate (Na$_2$SO$_4$), filtered and concentrated. The residue was purified by silica gel flash chromatography to give subtitled compound (673 mg).

APCI-MS: m/z 150 (MH$^+$). $^1$H-NMR (acetone-d$_6$ 400 MHz): δ 9.55 (br.s, 1H); 7.36 (m, 1H); 7.02 (d, J=8.3 Hz, 1H); 6.68 (d, J=7.8 Hz, 1H); 2.60 (s, 3H).

(ii) 4-({4-[1-(4-Chlorobenzyl)-4-piperidinyl]-2-morpholinyl}methoxy)-2-methyl-1,3-benzoxazole APCI-MS: m/z 456 (MH$^+$).

EXAMPLE-23

4-[1-(4-Chlorobenzyl)-4-piperidinyl]-2-[(2,4-dichlorophenoxy)methyl]morpholine

APCI-MS: m/z 469 (MH$^+$).

EXAMPLE-24

N-[2-({4-[1-(4-Chlorobenzyl)-4-piperidinyl]-2-morpholinyl}methoxy)phenyl]urea

APCI-MS: m/z 459 (MH$^+$).

EXAMPLE-25

N-[2-({4-[1-(4-Chlorobenzyl)-4-piperidinyl]-2-morpholinyl}methoxy)phenyl]-N'-ethylurea (i) N-Ethyl-N'-(2-hydroxyphenyl)urea A solution of 1-isocyanato-2-methoxybenzene (0.32 g, 2.15 mmol) and ethylamine (1 mL) in dichloromethane (15 mL) was stirred at room temperature for 2 days. Then the volatiles were removed in vacuo. The residue was redissolved in dichloromethane (15 mL), and boron tribromide (BBr$_3$) (1 M in dichloromethane (CH$_2$Cl$_2$), 6.5 ml, 6.5 mmol) was added dropwise via syringe under nitrogen. After stirring for 1 h the reaction mixture was diluted with dichloromethane and washed 3 times with water. The product was purified by HPLC (Kromasil column; eluant:acetonitrile+0.1% trifluoroacetic acid (TFA)/water+0.1% TFA) to give subtitle compound (167 mg).

APCI-MS: m/z 181 (MH$^+$). $^1$H-NMR (400 MHz, DMSO-d$_6$): δ 7.90 (br. s, 1H), 7.82 (dd, 1H, J=10.0, J=2.4).), 6.6–6.9 (m, 3H), 3.01 (quart, 2H, $^3$J=9.6) 1.05 (t, 3H, $^3$J=9.6).

(ii) N-[2-({4-[1-(4-Chlorobenzyl)-4-piperidinyl]-2-morpholinyl}methoxy)phenyl]-N'-ethylurea APCI-MS: m/z 487 (MH$^+$).

EXAMPLE-26

N'-[2-({4-[1-(4-Chlorobenzyl)-4-piperidinyl]-2-morpholinyl}methoxy)phenyl]-N,N-dimethylurea (i) N'-(2-hydroxyphenyl)-N,N-dimethylurea The subtitled compound was prepared using the procedure as described for Example 25 for N-ethyl-N'-(2-hydroxyphenyl)urea from 1-isocyanato-2-methoxybenzene and dimethylamine (2M solution in THF). Yield 54%.

APCI-MS: m/z 181 (MH$^+$). $^1$H-NMR (400 MHz, DMSO-d$_6$): δ 7.78 (br. s, 1H), 7.49 (dd, 1H, J=10.4, J=2.4).), 6.7–7.0 (m, 3H), 2.97 (s, 6H).

(ii) N'-[2-({4-[1-(4-Chlorobenzyl)-4-piperidinyl]-2-morpholinyl}methoxy)phenyl]-N,N-dimethylurea APCI-MS: m/z 487 (MH$^+$).

EXAMPLE-27

8-({4-[1-(4-Chlorobenzyl)-4-piperidinyl]-2-morpholinyl}methoxy)-3,4-dihydro-2(1H)-quinoline (i) 3-Chloro-N-(2-hydroxyphenyl)propanamide To a stirred solution of 2-aminophenol (2.18 g, 20 mmol) in acetone (20 mL) a solution of 3-chloropropionyl chloride (1.28 g, 0.87 mL, 10 mmol) in acetone (20 mL) was added dropwise. After the addition was completed, the reaction mixture was stirred at room temperature for 0.5 h and then diluted with water (50 mL). Acetone was removed in vacuo, the precipitate formed was collected by filtration, washed with water, and dried to give the subtitle compound (1.53 g, 77%).

APCI-MS: m/z 200 (MH$^+$) $^1$H-NMR (400 MHz, DMSO-4): δ 9.75 (s, 1H), 9.37 (s, 1H), 7.77 (d, 1H), 6.7–7.0 (m, 3H), 3.86 (t, 2H, $^3$J=7.2), 2.92 (t, 2H, $^3$J=6.0).

(ii) 8-Hydroxy-3,4-dihydro-2(1H)-quinolinone

A mixture of 3-chloro-N-(2-hydroxyphenyl)propanamide (0.25 g, 1.25 mmol) and aluminium chloride (AlCl$_3$) (0.5 g) was heated with stirring at 130–135° C. for 5 h. After cooling to room temperature, the reaction mixture was quenched with water (3 ml), and extracted with ethyl acetate (3×5 ml). Evaporation of the solvent and flash chromatography of the residue on silica gel with ethyl acetate/heptane (1:1) afforded colourless crystals of the subtitled compound (95 mg, 46.5%).

APCI-MS: m/z 164 (MH$^+$). $^1$H-NMR (400 MHz, DMSO-d$_6$): δ 9.64 (s, 1H), 8.76 (s, 1H), 6.6–6.8 (m, 3H), 2.83 (t, 2H, $^3$J=7.2), 2.43 (t, 2H, $^3$J=7.2).

(iii) 8-({4-[1-(4-Chlorobenzyl)-4-piperidinyl]-2-morpholinyl}methoxy)-3,4-dihydro-2(1H)quinoline
APCI-MS: m/z 470 (MH$^+$).

EXAMPLE-28

N-Benzyl-2-({4-[1-(4-chlorobenzyl)-4-piperidinyl]-2-morpholinyl}methoxy)aniline (i) 2-(Benzylamino)phenol To a stirred mixture of 2-aminophenol (3.0 g, 27.5 mmol), potassium carbonate (6.0 g, 43.4 mmol) and DMF (25 mL) 1-(bromomethyl)benzene (3.75 mL, 31.3 mmol) was added. The mixture was stirred at 60° C. overnight. Purification by preparative HPLC (Kromasil C$_{18}$; eluant:acetonitrile+0.1% TFA/water+0.1% TFA) gave the subtitled compound (1.82 g, 33%).

APCI-MS: m/z 200 (MH$^+$). $^1$H-NMR (400 MHz, DMSO-d$_6$): δ 7.2–7.4 (m, 5H), 6.6–6.9 (m, 4H), 4.37 (s, 2H).

(ii) N-Benzyl-2-({4-[1-(4-chlorobenzyl)-4-piperidinyl]-2-morpholinyl}methoxy)aniline
APCI-MS: m/z 506 (MH$^+$).

EXAMPLE-29

4-({4-[1-(4-Chlorobenzyl)-4-piperidinyl]-2-morpholinyl}methoxy)-2-methyl-1,3-benzoxazole (i) N-(2,6-dihydroxyphenyl)acetamide A mixture of 2-nitro-1,3-benzenediol (1.55 g 10 mmol), acetic anhydride (1.59 g, 1.47 mL, 15 mmol) and 10% palladium on charcoal (0.3 g) in methanol (100 mL) was stirred in the atmosphere of hydrogen at atmospheric pressure for 2 h. The catalyst was filtered through celite, the solvent evaporated in vacuo. The oily residue was treated with dichloromethane to afford colourless crystals, which were collected by filteration and dried to give the subtitle compound (1.09 g, 65%).

APCI-MS: m/z 168 (MH$^+$). $^1$H-NMR (400 MHz, DMSO-d$_6$): δ 9.34 (br. s, 1H), 6.87 (t, 1H, J=8.0), 6.34 (d, 2H, J=8.0), 2.10 (s, 3H).

(ii) 2-Methyl-1,3-benzoxazol-4-ol

N-(2,6-dihydroxyphenyl)acetamide was heated at 200° C. for 0.5 h. After cooling to room temperature, the product was purified by flash chromatography on silica gel (ethyl acetae/heptane, 1:1) to afford the subtitled compound as colourless crystals (0.77 g, 79%).

APCI-MS:m/z 150 (MH$^+$) $^1$H-NMR (400 MHz, DMSO-d$_6$): δ 10.15 (br. s, 1H), 7.11 (t, 1H, J=8.0), 7.04 (d, 1H, J=8.0), 6.70 (d, 1H, J=8.0), 2.56 (s, 3H).

(iii) 4-(14-[1-(4-Chlorobenzyl)-4-piperidinyl]-2-morpholinyl}methoxy)-2-methyl-1,3-benzoxazole
APCI-MS: m/z 456 (MH$^+$).

EXAMPLE-30

4-[1-(4-Chlorobenzyl)-4-piperidinyl]-2-{[2-(2-methyl)-2H-1,2,3,4-tetrazol-5-yl)phenoxy]methyl}morpholine (i) 2-(2H-1,2,3,4-Tetrazol-5-yl)phenol A stirred mixture of 2-cyanophenol (2.38 g, 20 mmol), sodium azide (3.9 g, 60 mmol) and ammonium chloride (1.39 g, 26 mmol) in dry DMF (10 mL) was heated at 130° C. for 48 h. After cooling to room temperature, the raction mixture was poured into water (100 mL), and the solution acidified with 6 N hydrochloric acid to pH 1. The precipitate formed was collected by filtration, and dried to give subtitled compound (3.14 g, 97%).

APCI-MS: m/z 163 (MH$^+$). $^1$H-NMR (400 MHz, DMSO-d$_6$): δ 8.01 (d, 1H, J=10.0), 7.25 (t, 1H, J=10.0), 7.0–7.2 (m, 2H).

(ii) 2-(2-Methyl-2H-1,2,3,4-tetraazol-5-yl)phenol

To a stirred solution of 2-(2H-1,2,3,4-tetrazol-5-yl)phenol (0.486 g, 3 mmol) and sodium hydroxide (NaOH) (72 mg, 3 mmol) in water (15 mL) a solution of tetrabutylammonium chloride (83 mg, 0.3 mmol) was added. The mixture was stirred for 5 min, then methyl iodide (0.425 g, 0.187 mL, 3 mmol) was added, and the mixture was stirred for 6 days. The organic layer was then separated, washed with water (2×15 mL), and dried. Evaporation of solvent and flash chromatography on silica gel (ethyl acetate/heptane, 1:1) afforded the subtitle compound (0.257 g, 49%).

APCI-MS: m/z 177 (MH$^+$) $^1$H-NMR (400 MHz, CDCl$_3$): δ 9.69 (s, 1H), 8.04 (dd, 1H, J=7.9, J=1.7), 7.38 (dt, 1H, J=7.3, J=1.7), 7.09 (dd, 1H, J=8.4, J=0.9), 7.00 (dt, 1H, J=7.5, J=1.0), 4.45 (s, 3H).

(iii) 4-[1-(4-Chlorobenzyl)-4-piperidinyl]-2-([2-(2-methyl)-2H-1,2,3,4-tetrazol-5-yl)phenoxy]methyl}morpholine
APCI-MS: m/z 483 (MH$^+$).

EXAMPLE-31

4-[1-(4-Chlorobenzyl)-4-piperidinyl]-2-[(3,5-difluorophenyl)methyl]morpholine APCI-MS: m/z 437 (MH$^+$).

THP-1 Chemotaxis Assay

Introduction

The assay measured the chemotactic response elicited by MIP-1α chemokine in the human monocytic cell line THP-1. The compounds of the Examples were evaluated by their ability to depress the chemotactic response to a standard concentration of MIP-1α chemokine.

Methods

Culture of THP-1 Cells

Cells were thawed rapidly at 37° C. from frozen aliquots and resuspended in a 25 cm flask containing 5 ml of RPMI-1640 medium supplemented with Glutamax and 10% heat inactivated fetal calf serum without antibiotics (RPMI+10% HIFCS). At day 3 the medium is discarded and replaced with fresh medium.

THP-1 cells are routinely cultured in RPMI-1640 medium supplemented with 10% heat inactivated fetal calf serum and glutamax but without antibiotics. Optimal growth of the cells requires that they are passaged every 3 days and that the minimum subculture density is 4×10+5 cells/ml.

Chemotaxis Assay

Cells were removed from the flask and washed by centrifugation in RPMI+10% HIFCS+glutamax. The cells were then resuspended at 2×10+7 cells/ml in fresh medium (RPMI+10% HIFCS+glutamax) to which was added calcein-AM (5 µl of stock solution to 1 ml to give a final concentration of ×10$^{-6}$M). After gentle mixing the cells were incubated at 37° C. in a CO$_2$ incubator for 30 minutes. The cells were then diluted to 50 ml with medium and washed twice by centrifugation at 400×g. Labelled cells were then resuspended at a cell concentration of 1×10+7 cells/ml and incubated with an equal volume of MIP-1α antagonist (10$^{-10}$M to 10$^{-6}$M final concentration) for 30 minutes at 37° C. in a humidified CO$_2$ incubator.

Chemotaxis was performed using Neuroprobe 96-well chemotaxis plates employing 8 µm filters (cat no. 101-8). Thirty microliters of chemoattractant supplemented with various concentrations of antagonists or vehicle were added to the lower wells of the plate in triplicate. The filter was then carefully positioned on top and then 25 µl of cells preincubated with the corresponding concentration of antagonist or vehicle were added to the surface of the filter. The plate was then incubated for 2 hours at 37° C. in a humidified CO$_2$ incubator. The cells remaining on the surface were then removed by adsorption and the whole plate was centrifuged at 2000 rpm for 10 minutes. The filter was then removed and the cells that had migrated to the lower wells were quantified by the fluorescence of cell associated calcein-AM. Cell migration was then expressed in fluorescence units after subtraction of the reagent blank and values were standardized to % migration by comparing the fluorescence values with that of a known number of labelled cells. The effect of antagonists was calculated as % inhibition when the number of migrated cells were compared with vehicle.

The invention claimed is:

1. A compound of general formula

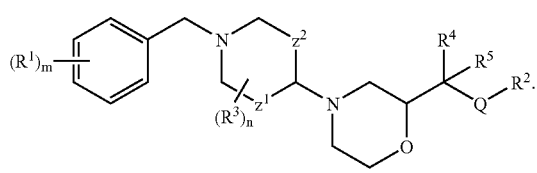

(I)

wherein
 m is 0, 1, 2 or 3;
 each $R^1$ independently represents halogen, cyano, nitro, carboxyl, hydroxyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —NR$^6$R$^7$, $C_3$–$C_6$ cycloalkylamino, $C_1$–$C_6$ alkylthio, $C_1$–$C_6$ alkylcarbonyl, $C_1$–$C_6$ alkylcarbonylamino, sulphonamido, $C_1$–$C_6$ alkylsulphonyl, —C(O)NR$^8$R$^9$, —NR$^{10}$C(O)—(NH)$_p$R$^{11}$, phenyl, or $C_1$–$C_6$ alkyl optionally substituted by at least one substituent selected from carboxyl and $C_1$–$C_6$ alkoxycarbonyl;
 $Z^1$ represents a bond or a group (CH$_2$)$_q$ where q is 1 or 2;
 $Z^2$ represents a group CH$_2$, with the proviso that $Z^1$ and $Z^2$ do not both simultaneously represent a bond;
 Q represents an oxygen or sulphur atom;
 $R^2$ represents an unsaturated 5- to 10-membered cyclic or aryl ring system, the ring system being optionally substituted by at least one substituent selected from halogen, cyano, oxo, nitro, carboxyl, hydroxyl, $C_2$–$C_6$ alkenyl, $C_3$–$C_6$ cycloalkyl, $C_1$–$C_6$ alkoxy, $C_1$–$C_6$ alkoxycarbonyl, $C_1$–$C_6$ haloalkyl, $C_1$–$C_6$ haloalkoxy, —NR$^{12}$R$^{13}$, $C_3$–$C_6$ cycloalkylamino, $C_1$–$C_6$ alkylthio, $C_1$–$C_6$ alkylcarbonyl, phenylcarbonyl, $C_1$–$C_6$ alkylcarbonylamino, sulphonamido, $C_1$–$C_6$ alkylsulphonyl, —C(O)NR$^{14}$R$^{15}$, $C_1$–$C_6$ alkoxycarbonylC$_1$–$C_6$alkyl, phenyl, methyltetrazolyl, —NHSO$_2$CH$_3$, —NHC(O)NR$^{16}$R$^{17}$, —OC(O)NR$^{18}$R$^{19}$, —OCH$_2$C(O)NR$^{20}$R$^{21}$, —NHC(O)OR$^{22}$, —NHC(O)R$^{23}$, and $C_1$–$C_6$ alkyl itself optionally substituted by at least one substituent selected from carboxyl and $C_1$–$C_6$ alkoxycarbonyl;
 n is 0, 1 or 2;
 each $R^3$ independently represents a $C_1$–$C_6$ alkyl, $C_1$–$C_6$ alkoxycarbonyl, —CH$_2$OH or carboxyl group;
 $R^4$ and $R^5$ each independently represent a hydrogen atom or a $C_1$–$C_6$ alkyl group;
 $R^6$ and $R^7$ each independently represent a hydrogen atom or a $C_1$–$C_6$ alkyl group, or $R^6$ and $R^7$ together with the nitrogen atom to which they are attached form a 4- to 7-membered saturated heterocycle;
 $R^8$ and $R^9$ each independently represent a hydrogen atom or a $C_1$–$C_6$ alkyl group optionally substituted by at least one $C_1$–$C_6$ alkoxycarbonyl;
 p is 0 or 1;
 $R^{10}$ represents a hydrogen atom or a $C_1$–$C_6$ alkyl group;
 $R^{11}$ represents a hydrogen atom, or a $C_1$–$C_6$ alkyl group optionally substituted by at least one substituent selected from carboxyl, $C_1$–$C_6$ alkoxy and $C_1$–$C_6$ alkoxycarbonyl;
 $R^{12}$ and $R^{13}$ each independently represent a hydrogen atom, a phenyl group, or a $C_1$–$C_6$ alkyl group optionally substituted by at least one substituent selected from carboxyl and $C_1$–$C_6$ alkoxycarbonyl, or $R^{12}$ and $R^{13}$ together with the nitrogen atom to which they are attached form a 4- to 7-membered saturated heterocycle;
 $R^{14}$ and $R^{15}$ each independently represent a hydrogen atom, a phenyl group, a $C_3$–$C_6$ cycloalkyl group, or a $C_1$–$C_6$ alkyl group optionally substituted by at least one substituent selected from carboxyl and $C_1$–$C_6$ alkoxycarbonyl, or $R^{14}$ and $R^{15}$ together with the nitrogen atom to which they are attached form a 4- to 7-membered saturated heterocycle;
 $R^{16}$ and $R^{17}$ each independently represent a hydrogen atom, or a $C_1$–$C_6$ alkyl group optionally substituted by at least one substituent selected from carboxyl and $C_1$–$C_6$ alkoxycarbonyl, or $R^{16}$ and $R^{17}$ together with the nitrogen atom to which they are attached form a 4- to 7-membered saturated heterocycle;
 $R^{18}$ and $R^{19}$ each independently represent a hydrogen atom, or a $C_1$–$C_6$ alkyl group optionally substituted by at least one substituent selected from carboxyl and $C_1$–$C_6$ alkoxycarbonyl, or $R^{18}$ and $R^{19}$ together with the nitrogen atom to which they are attached form a 4- to 7-membered saturated heterocycle;
 $R^{20}$ and $R^{21}$ each independently represent a hydrogen atom, or a $C_1$–$C_6$ alkyl group optionally substituted by at least one substituent selected from carboxyl and $C_1$–$C_6$ alkoxycarbonyl, or $R^{20}$ and $R^{21}$ together with the nitrogen atom to which they are attached form a 4- to 7-membered saturated heterocycle;
 $R^{22}$ represents a hydrogen atom, or a $C_1$–$C_6$ alkyl group optionally substituted by at least one substituent selected from carboxyl and $C_1$–$C_6$ alkoxycarbonyl;
 $R^{23}$ represents a group $C_1$–$C_6$ alkyl, $C_2$–$C_6$ alkenyl, $C_3$–$C_6$ cycloalkyl, adamantyl, $C_5$–$C_6$ cycloalkenyl, phenyl or a saturated or unsaturated 5- to 10-membered heterocyclic ring comprising at least one ring heteroatom selected from the group consisting of: nitrogen, oxygen and sulphur, each group being optionally substituted by at least one substituent selected from the group consisting of: nitro, hydroxyl, oxo, halogen, carboxyl, $C_1$–$C_6$ alkyl, $C_1$–$C_6$ alkoxy, $C_1$–$C_6$ alkylthio, $C_1$–$C_6$ alkylcarbonyl, $C_1$–$C_6$ alkoxycarbonyl, phenyl and —NHC(O)—$R^{24}$; and $R^{24}$ represents a $C_1$–$C_6$ alkyl, amino (—$NH_2$) or phenyl group;

or a pharmaceutically acceptable salt or solvate thereof.

2. A compound according to claim 1, wherein each $R^1$ independently represents halogen, cyano, nitro, $C_1$–$C_6$ alkoxy, $C_1$–$C_6$ alkylcarbonyl or $C_1$–$C_6$ alkylcarbonylamino.

3. A compound according to claim 1, wherein $Z^1$ and $Z^2$ both represent $CH_2$.

4. A compound according to claim 1, wherein Q represents an oxygen atom.

5. A compound according to claim 1, wherein the unsaturated 5- to 10-membered ring system in $R^2$ is selected from phenyl, naphthyl, 1,3-benzodioxolyl, pyrazolyl, thienyl, oxazolyl, imidazolyl, pyridinyl, pyridopyrrolyl, benzimidazolyl, indazolyl, benzothiazolyl, quinolinyl, benzoxazolyl, benzisoxazolyl, tetrahydroquinolinyl, thiazolyl and benzotriazolyl.

6. A compound according to claim 1, wherein the unsaturated 5- to 10-membered ring system in $R^2$ is optionally substituted by at least one substituent selected from halogen, cyano, oxo, $C_1$–$C_6$ alkyl, $C_2$–$C_6$ alkenyl, $C_1$–$C_6$ alkoxy, —$NR^{12}R^{13}$, $C_1$–$C_6$alkylcarbonyl, phenylcarbonyl, methyltetrazolyl, —C(O)$NR^{14}R^{15}$, —NHC(O)$NR^{16}R^{17}$ and —NHC(O)$R^{23}$.

7. A compound according to claim 1 being selected from:
N-[2-({4-[1-(4-Chlorobenzyl)-4-piperidinyl]-2-morpholinyl}methoxy)phenyl]acetamide,
1-[3-({4-[1-(4-Chlorobenzyl)-4-piperidinyl]-2-morpholinyl}methoxy)phenyl]-1-ethanone,
4-[1-(4-Chlorobenzyl)-4-piperidinyl]-2-[(2-naphthyloxy)methyl]morpholine,
4-[1-(4-Chlorobenzyl)-4-piperidinyl]-2-[(3-methoxyphenoxy)methyl]morpholine,
3-({4-[1-(4-Chlorobenzyl)-4-piperidinyl]-2-morpholinyl}methoxy)benzonitrile,
4-[1-(4-Chlorobenzyl)-4-piperidinyl]-2-[3,4-difluorophenoxy)methyl]morpholine,
4-[1-(4-Chlorobenzyl)-4-piperidinyl]-2-[(2-ethoxyphenoxy)methyl]morpholine,
4-[1-(4-Chlorobenzyl)-4-piperidinyl]-2-[(2-chlorophenoxy)methyl]morpholine,
N-[2-({(2S)-4-[1-(4-Chlorobenzyl)-4-piperidinyl]morpholinyl}methoxy)phenyl]-acetamide,
N-[2-({(2R)-4-[1-(4-Chlorobenzyl)-4-piperidinyl]morpholinyl}methoxy)phenyl]-acetamide,
N-[2{4-[1-(4-Chlorobenzyl)-4-piperidinyl]-2-morpholinyl}methoxy)phenyl]-benzamide,
2-({4-[1-(4-Chlorobenzyl)-4-piperidinyl]-2-morpholinyl}methoxy)-N-phenyl-benzamide.
2-({4-[1-(4-Chlorobenzyl)-4-piperidinyl]-2-morpholinyl}methoxy)-N-methyl-benzamide,
2-[1-(4-Chlorobenzyl)-4-piperidinyl]-2-[(1-naphthyloxy)methyl]morpholine,
[3-({4-[1-(4-Chlorobenzyl)-4-piperidinyl]-2-morpholinyl}methoxy)-phenyl]-(phenyl)methanone,
4-[1-(4-Chlorobenzyl)-4-piperidinyl]-2-({2-[(E)-1-propenyl}phenoxy)-methyl)-morpholine,
2-({4-[1-(4-Chlorobenzyl)-4-piperidinyl]-2-morpholinyl}methoxy)-N-cyclopropyl-benzamide,
4-[1-(4-Chlorobenzyl)-4-piperidinyl]-2-[(2-iodophenoxy)methyl]morpholine,
4-[1-(4-Chlorobenzyl)-4-piperidinyl]-2-[(4-chloro-2-isopropyl-5-methylphenoxy)-methyl]morpholine,
4-[1-(4-Chlorobenzyl)-4-piperidinyl]-2-[(2,4-dichlorophenoxy)methyl]morpholine,
N-[2-({4-[1-(4-Chlorobenzyl)-4-piperidinyl]-2-morpholinyl}methoxy)phenyl]urea,
N-[2-({4-[1-(4-Chlorobenzyl)-4-piperidinyl]-2-morpholinyl}methoxy)phenyl]-N'-ethylurea,
N'-[2-({4-[1-(4-Chlorobenzyl)-4-piperidinyl]-2-morpholinyl}methoxy)phenyl]-N,N-dimethylurea,
N-Benzyl-2-({4-[1-(4-chlorobenzyl)-4-piperidinyl]-2-morpholinyl}methoxy)aniline,
4-[1-(4-Chlorobenzyl)-4-piperidinyl]-2-{[2-(2-methyl)-2H-1,2,3,4-tetrazol-5-yl)phenoxy]methyl}morpholine, and
4-[1-(4-Chlorobenzyl)-4-piperidinyl]-2-[(3,5-difluorophenyl)methyl]morpholine
or a pharmaceutically acceptable salt or solvate of any one thereof.

8. A process for the preparation of a compound of formula (I) as defined in claim 1 which comprises
(i) when Q represents an oxygen or sulphur atom, reacting a compound of general formula

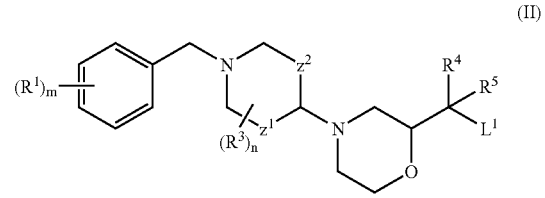

(II)

wherein $L^1$ represents a leaving group and m, n, $Z^1$, $Z^2$, $R^1$, $R^3$, $R^4$ and $R^5$ are as defined in formula (I), with a compound of general formula $R^2$-Q'H    (III)

wherein Q' represents an oxygen or sulphur atom or a group NH and $R^2$ is as defined in formula (I); or
(ii) when Q represents a group $CH_2$, reacting a compound of general formula $R^2$—$CH_2$-$L^2$    (IV)

wherein $L^2$ represents a halogen atom and $R^2$ is as defined in formula (I), with an alkali metal, followed by reaction with a compound of formula (II) as defined in (i) above;

and optionally after (i) or (ii) forming a pharmaceutically acceptable salt or solvate of the compound of formula (I) obtained.

9. A pharmaceutical composition comprising a compound of formula (I), or a pharmaceutically acceptable salt or solvate thereof, as claimed in claim 1 in association with a pharmaceutically acceptable adjuvant, diluent or carrier.

10. A process for the preparation of a pharmaceutical composition which comprises mixing a compound of formula (I), or a pharmaceutically acceptable salt or solvate thereof, as claimed in claim 1 with a pharmaceutically acceptable adjuvant, diluent or carrier.

11. A method for treatment of rheumatoid arthritis, chronic obstructive pulmonary disease, asthma or multiple sclerosis in a patient, the method comprising:

administering to the patient a compound of formula (I), or a pharmaceutically acceptable salt or solvate thereof, as claimed in claim 1.

12. A method for treatment of rheumatoid arthritis in a patient, the method comprising:
   administering to the patient a compound of formula (I), or a pharmaceutically acceptable salt or solvate thereof, as claimed in claim 1.

13. A method for treatment of chronic obstructive pulmonary disease in a patient, the method comprising:
   administering to the patient a compound of formula (I), or a pharmaceutically acceptable salt or solvate thereof, as claimed in claim 1.

14. A method for treatment of asthma in a patient, the method comprising:
   administering to the patient a compound of formula (I), or a pharmaceutically acceptable salt or solvate thereof, as claimed in claim 1.

15. A method for treatment of multiple sclerosis in a patient, the method comprising:
   administering to the patient a compound of formula (I), or a pharmaceutically acceptable salt or solvate thereof, as claimed in claim 1.

* * * * *